(12) United States Patent
Pardo Cortes et al.

(10) Patent No.: US 11,788,090 B2
(45) Date of Patent: Oct. 17, 2023

(54) PREVENTION AND/OR TREATMENT OF INFLAMMATORY SKIN DISEASE

(71) Applicant: Conopco, Inc., Englewood Cliffs, NJ (US)

(72) Inventors: Luba Milena Pardo Cortes, Rotterdam (NL); Rebecca Susan Ginger, Loughborough (GB); David Andrew Gunn, St Neots (GB); Tamarius Edmond Christoffel Nijsten, Antwerp (BE); Martijn Gerard Hendrik Sanders, Rotterdam (NL); Adrian Michael Smith, Corby (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 538 days.

(21) Appl. No.: 16/611,847

(22) PCT Filed: May 3, 2018

(86) PCT No.: PCT/EP2018/061414
§ 371 (c)(1),
(2) Date: Nov. 7, 2019

(87) PCT Pub. No.: WO2018/206409
PCT Pub. Date: Nov. 15, 2018

(65) Prior Publication Data
US 2020/0063139 A1 Feb. 27, 2020

(30) Foreign Application Priority Data
May 8, 2017 (EP) .................................... 17169956

(51) Int. Cl.
| | |
|---|---|
| *C12N 15/113* | (2010.01) |
| *A61K 8/04* | (2006.01) |
| *A61Q 5/00* | (2006.01) |
| *A61Q 5/02* | (2006.01) |
| *A61Q 5/12* | (2006.01) |
| *C12Q 1/48* | (2006.01) |
| *G01N 33/68* | (2006.01) |

(52) U.S. Cl.
CPC .......... *C12N 15/1137* (2013.01); *A61K 8/042* (2013.01); *A61Q 5/006* (2013.01); *A61Q 5/02* (2013.01); *A61Q 5/12* (2013.01); *C12Q 1/485* (2013.01); *C12Y 207/11001* (2013.01); *G01N 33/6881* (2013.01); *C12N 2310/14* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 6,184,215 B1 | 6/2001 | Elias et al. | |
| 2004/0228884 A1 | 11/2004 | Gupta | |
| 2012/0039812 A1 | 2/2012 | Holsboer et al. | |
| 2014/0243392 A1* | 8/2014 | Ochiya | A61B 5/4504 |
| | | | 435/6.12 |

FOREIGN PATENT DOCUMENTS

| | | | | |
|---|---|---|---|---|
| WO | WO-9942463 A1 * | 8/1999 | ........... | C07D 231/12 |
| WO | WO03003004 | 9/2003 | | |
| WO | WO2016160721 | 6/2016 | | |
| WO | WO2016073955 | 12/2016 | | |

OTHER PUBLICATIONS

Sun et al. Molecular Biology vol. 40, pp. 724-731 (Year: 2006).*
Nelson Molecular and Cellular Endocrinology 406, 73-80 (Year: 2006).*
Turner et al.; Stratum corneum dysfunction in dandruff; International Journal of Cosmetic Science; May 2012; pp. 298-306 (also as XP055114488); 34.
Ginger et al.; Characterisation of dandruff scalp transcriptome uncovers shared features with psoriasis ; J. Invest. Dermatol. (Abstracts); S1-S17 (abstracts, p. 14); 135, 2015.
Stuart et al.; Genome-wide associations analysis identifies three psoriasis susceptibility loci; Nature Genetics; 2010; 1000-1006; 42 (11).
Chatzikokkinou, et al.; Seborrheic Dermatitis—An Early and Common Skin ; Acta Dermatovenerol Croat; 2008; 226-230; 16(4).
Mastrolonardo, et al.; Seborrheic dermatitis, increased sebum excretion, and Parkinson's disease: a survey of (im)possible links; Medical Hypotheses; 2003; 907-911; 60(6).
Schwartz, et al.; A Comprehensive Pathophysiology of Dandruff and Seborrheic ; Acta Derm Venereol; 2013; 131-137; 93.
Dawson; Malassezia globosa and restricta: Breakthrough, Understanding of the Etiology and Treatment, of Dandruff and Seborrheic Dermatitis through Whole-Genome Analysis; J. Investig. Dermatol. Symp. Proc.; 2007; 15-19; 12(2).
Gupta et al.; Seborrheic dermatitis; European Academy of Dermatory and Venereology; 2004; pp. 13-26; 18.
Wang, et al.; Seborrheic dermatitis: lifetime detection rates; Journal of the European Academy of Dermatology and Venereology " 2011 European Academy of Dermatology and Venereology; 2012; 523-529; 26.
Szepietowski et al.,; Quality of life in patients suffering from seborrheic dermatitis: influence of age, gender and education level; Mycoses; 2008; 357-363; 52.
Lally et al.; Seborrheic dermatitis in renal transplant recipients; JEADV; 2010; pp. 561-564; 24.

(Continued)

*Primary Examiner* — Brian Whiteman
(74) *Attorney, Agent, or Firm* — Foley & Lardner LLP (57) ABSTRACT

Disclosed is a substance which down-regulates the activity of a MAST gene, or the activity of a transcription or translation product of a MAST gene, for use in the prevent and/or treatment of an inflammatory skin condition in a mammalian subject.

19 Claims, 3 Drawing Sheets

Specification includes a Sequence Listing.

(56) References Cited

OTHER PUBLICATIONS

Li et at.; Hit-to-lead optimization and kinase selectivity of imidazo[1,2-a]quinoxalin-4-amine derived JNK1 inhibitors; Bioorganic & Medicinal Chemistry Letters; 2013; pp. 5217-52222; vol. 23; Elsevier.
IPRP2 in PCTEP2018061414; Apr. 3, 2019; World Intellectual Property Org. (WIPO).
Search Report and Written Opinion in PCTEP2018061414.
Borregaard, Jeanette et al.; Evaluation of the effect of the specific CCR1 antagonist CP-481715 on the clinical and cellular responses observed following epicutaneous nickel challenge in human subjects; Contact Dermatitis; Jan. 1, 2008; pp. 212-219, XP055415503; vol. 59, No. 4.
Bickers et al.; The burden of skin diseases: 2004; Journal of the American Academy of Dermatol; Sep. 1, 2006; pp. 490-500, XP005603426; vol. 55, No. 3.
Hofman et al.; The Rotterdam Study: 2016 objectives and design update; European Journal of Epidemiology; Sep. 19, 2015; pp. 661-708, XP035537665; vol. 30, No. 8.
Borda, Luis J. et al.; Seborrheic Dermatitis and Dandruff: A Comprehensive Review; J Clin Investig Dermatol; Dec. 1, 2015; pp. 1-22, XP055415062; vol. 3(2).
Search Report and Written Opinion in EP17169956; dated Oct. 30, 2017.
Palamaras et al.; Seborrheic dermatitis: lifetime detection rates; Journal of the European Academy of Dermatology and Venereology; 2012; pp. 523-529; 26(4).
Changgui Lan; Chapters Skin Inflammation; Theory and Practice of Dermatology; May 31, 2009 pp. 227-228, with English translation; Sichuan Science and Technology Press; China.
Yu-Ping Dang et al.; The effect of TLR2 on the secretion of IFN-$\gamma$ and IL-8 from keratinocytes in dermatophyte infection; Modern Journal of Integrated Traditional Chinese and Western Medicine; Nov. 20, 2013; pp. 3695-3697, with English translation; No. 33; China.

\* cited by examiner

Fig. 1

```
CCCACTTTAC CAAGCAAGGT ATTAATTTTC TTCCTAGCAG AGGAAAGAGC TCAGTTCACT
GTATTCTCTT TCCTTTACA ACAGTTACAA CAACATTTGA TTCGTGATAT TTTAGTTGTA
GGTTGTTGAT TTAAAAATAC ACTTAGAAGG TGTGGAGCAC AGAGGAATAC AGGGCATGAT
TTTGTGTATT GACCTGTCAA CCCTGGTTAA CTAGCATGTC ACAAAAACAAG TTCTAAACTC
AAATACAGTA AATTATCCAG GTGGGATTCT GGCCACTTGT GATGAGTTAC GGATTTTGAT
TTGGATCATT CTTGCCCTAG CTTGGTAACA GGGGAGTGTA TTTATGTATT ATGAAATGTG
AGACCTTTTC AAATAGTATT ATGGTCATGT GTCACTCATG AATGGGGATA TGTTCTGAGA
AGCATGTCAT TAAGCAATTT TGTCATTTCG CAAACATCAT GGAGTGTACT TCTACAAACT
TAGATGGTGT AGCTTACTAC
R
TACCTAGGCT ATATGGTATA GCCTATTGCT ACTGGGCTAC AAACCTGTAT AGCTTGTTAC
TGTACTGAAT ACTGTAAGCA GTTGTAACAC AATCATAAGT ATTTTTATAT CTAAATGTAT
CCAAACATAG AAAAGGTACA GCAAAAATAT GGTATTATAA TCTTTTATAA TATATAATTA
TAATATATGT GGGCTGTGGT TGGTTGAAAC ATTATACAGC ACTGACTGTA TCTTAAATGG
TCAATAATTT TTACTTAAAG AAATCTTACT AGTTGATGGC TTCAAAGATT AGGCTCCCTC
TATAGGCCAC AGCCATCCCT TTGTTTCTTT TTGCATGTTC TTTTCTTTTT GAGAATGCTT
AAAATTATTA TTTCCTTATT TTTCAGCTAA TCTGCCCTTG TTCTTAAATGA AATATTATTT
CATTTAAAG AAATAGTGGT GTTTCTGGTC ATATGATTTT TCTGTTTTTT TAATTTTTAA
ATTTCTGCCA ATTTTGTTCA
```

| Derivative | A | B | C |
| --- | --- | --- | --- |
| 23 | Me | H | H |
| 19 | H | Me | H |
| 24 | Et | H | H |
| 25 | H | Et | H |
| 26 | $CH_2OH$ | H | H |
| 27 | H | $CH_2OH$ | H |
| 28 | H | $CH_2CH_2CH_3$ | H |
| 29 | H | iPr | H |
| 30 | H | Ph | H |
| 31 | H | $CH_2CH_2OH$ | H |
| 32 | H | $CH_2OCH_3$ | H |
| 33 | Me | Me | H |
| 34 | Et | Et | H |
| 35 | $CH_2CH_2$ | | H |
| 36 | $CH_2CH_2CH_2$ | | H |
| 37 | $CH_2CH_2CH_2CH_2$ | | H |
| 38 | $CH_2CH_2CH_2CH_2CH_2$ | | H |
| 39 | $CH_2CH_2CH_2CH_2CH_2CH_2$ | | H |
| 40 | $CH_2CH_2$ | | Me |
| 41 | $CH_2CH_2$ | | Cl |
| 42 | $CH_2CH_2$ | | F |

PREVENTION AND/OR TREATMENT OF INFLAMMATORY SKIN DISEASE

CROSS-REFERENCE TO RELATED APPLICATIONS

This application is a U.S. national phase application under 35 U.S.C. § 371 of International Application No. PCT/EP2018/061414, filed on May 3, 2018, which claims priority to EP Patent Application No. 17169956.4, filed May 8, 2017, the entire disclosures of which are incorporated herein by reference in their entireties, for any and all purposes.

SEQUENCE LISTING

The instant application contains a Sequence Listing which has been submitted electronically in ASCII format and is hereby incorporated by reference in its entirety. Said ASCII copy, created on Nov. 7, 2019 is named T3297EP.txt and is 2 kilobytes in size.

FIELD OF THE INVENTION

The present invention relates to a substance for use in the prevention and/or treatment of an inflammatory skin condition in a mammalian subject, especially a human subject, and an assay method useful for identifying such substances.

BACKGROUND OF THE INVENTION

Seborrheic dermatitis (SD) is a common chronic inflammatory relapsing skin disease characterized by greasy scaling, mostly occurring in sebum-rich regions such as scalp, face and chest. The overall prevalence of SD is not well documented but it is estimated to be approximately 4% (Gupta A K, Bluhm R. Seborrheic dermatitis. J Eur Acad Dermatol. 2004; 18(1):13-26; Palamaras et al., Seborrheic dermatitis: lifetime detection rates. J Eur Aced Dermatol Venereol. 2012; 26(4):524-6). SD has a high socioeconomic impact, exceeding $1.4 billion in the United States in 2004. Despite the relatively high burden of disease, remarkably little is known about the pathogenesis of SD (Bickers et al., J Am Acad Dermatol. 2006; 55(3):490-500; Szepietowski et al., Mycoses. 2009; 52(4):357-63).

Dandruff is a common condition involving the formation of skin flakes, and the symptoms are often similar in appearance to those of SD. For this reason, the two terms are sometimes used interchangeably, with SD of the scalp being thought of as severe dandruff. However, for present purposes, the two conditions are regarded as different and the following distinctions are recognized between dandruff and SD: (i) dandruff only ever occurs on the scalp, whilst SD can occur on other parts of the body, such as the face and chest; (ii) dandruff is characterized by patches of loosely adherent small skin flakes, grey or white in colour, often accompanied by itching, whilst in SD skin flakes are profuse, often appearing as adherent mounds, which are greasy yellow in colour; (iii) SD may be accompanied by visible redness (erythema) of the skin, which is never present in dandruff. Nevertheless, despite these distinctions, the two conditions do share many similarities.

Malassezia yeasts seem to play a significant role in the pathogenesis of SD, since eliminating the yeast gives an improvement of the disease. However, this yeast can be considered a commensal, which is present on the skin of both healthy as well as in affected individuals, indicating the influence of other factors (Dawson, J. Investig. Dermatol. Symp. Proc. 2007; 12(2):15-19). Host risk factors have been associated with SD, including dysfunction of the stratum corneum barrier, altered immune response to metabolites of Malassezia and increased sebaceous gland secretion (Turner et al., Int J Cosmet Sci. 2012; 34(4):298-306; Schwartz et al., Acta Derm Venereol. 2013; 93(2):131-7). In addition, SD is more common in males and has a remarkably high prevalence in Acquired Immune Deficiency Syndrome, transplant recipients and people suffering from Parkinson's disease (Mastrolonardo et al., Med Hypotheses. 2003; 60(6): 907-11; Lally et al., J Eur Acad Dermatol Venereol. 2010; 24(5):561-4, Chatzikokkinou et al., Acta Dermatovenerol Croat. 2008; 16(4):226-30). Environmental, lifestyle and hygiene factors have also been associated with SD, e.g. stress, climate, alcohol abuse and obesity (Gupta & Bluhm., 2004 cited above).

The genetic predisposition for SD has not been studied, resulting in the absence of candidate genes involved in the pathogensis of SD. However, it could be argued that SD shares several clinical features with other chronic inflammatory skin diseases, in particular with psoriasis (PSO) (sometimes coined 'sebopsoriasis') and atopic dermatitis (AD), which are much better characterized genetically (Genetics EA, Lifecourse Epidemiology Eczema C, Australian Asthma Genetics C, Australian Asthma Genetics Consortium A. Multi-ancestry genome-wide association study of 21,000 cases and 95,000 controls identifies new risk loci for atopic dermatitis. Nat Genet. 2015; Stuart et al. Nat Genet. 2010; 42(11):1000-4). Dysfunction of the skin barrier and an inadequate immune-mediated response to external stimuli are shared factors in the pathogenesis of these three skin diseases. In a recent study, an overlap in gene transcription profiles of scalp tissue of dandruff, AD and PSO was found, suggesting a possible shared genetic susceptibility (Ginger et al., J Invest Dermatol. 2015; 135, S1-S17). Whether the known gene variants of AD and PSO are also associated with SD is unknown.

The present invention aims to provide improvements in or relating to the prevention and/or treatment of inflammatory skin conditions and, more especially, the prevention and/or treatment of SD and/or dandruff.

SUMMARY OF THE INVENTION

In a first aspect, the invention provides a substance which down-regulates the activity of a MAST4 gene, or the activity of a transcription or translation product of a MAST4 gene, for use in the prevention and/or treatment of an inflammatory skin condition in a mammalian subject. (MAST=Microtuble-Associated Serine Threonine kinase).

In addition to the serine threonine kinase activity, MAST proteins have a protein-binding activity, mediated by a PDZ domain.

The activity of the MAST4 gene or gene product which is, directly or indirectly down-regulated may typically (but not necessarily) comprise the serine threonine kinase activity and/or the PDZ domain protein-binding activity.

In some embodiments, the substance may modulate the specific activity of the MAST4 gene or gene product (i.e. decrease the kinase activity per mg of MAST4 gene or gene product) or may modulate the activity by causing a decrease in the amount of MAST4 gene or MAST4 gene product. In other embodiments the substance may indirectly modulate the activity of the MAST4 protein by modulating an interaction between a MAST4 protein and one or more protein binding partners for MAST4 proteins.

As indicated above, MAST proteins comprise a PDZ domain. PDZ domains are present in proteins from a wide variety of sources (bacteria, yeasts, plants, insects and vertebrates). Typically they bind to the C-terminal amino acid residues of proteins or, less commonly, to internal peptide sequences of proteins.

The function of PDZ domains is often to localize cellular proteins and/or to regulate cellular pathways. Several hundred different PDZ domains have been identified and, whilst they exhibit considerable variety in terms of their amino acid sequence (about 80-90 residues in length), they generally comprise 4-6 β-strands, one short α helix and one long α helix, arranged in a compact globular structure.

The mammalian subject is preferably a human subject.

The inflammatory skin condition may be selected from the group consisting of: atopic dermatitis (AD), psoriasis (PSO), seborrheic dermatitis, dandruff, rosacea, and acne. Typically the inflammatory skin condition is a chronic inflammatory skin condition, and preferably comprises SD or dandruff.

Four MAST genes (MAST1, MAST2, MAST3 and MAST4) are known to be present in the human genome and are expressed, to various levels, in human skin. The compound modulates the activity of at least the MAST4 gene, or the activity of a transcription or translation product of the MAST4 gene. From their own experimental data, the inventors believe that the MAST4 gene is expressed in human skin at higher levels than any of the MAST 1-3 genes.

By way of explanation, the present inventors have found (as a result of a Genome Wide Association Study) that a single nucleotide polymorphism (SNP), mapping to an intronic region of the MAST4 gene, is strongly associated with seborrheic dermatitis to a statistically significant level. This presents the possibility that a compound which up- or down-regulates the activity of the MAST4 gene at the nucleic acid and/or polypeptide level, may exert a beneficial prophylactic and/or therapeutic effect on seborrheic dermatitis or a similar inflammatory skin condition, such as dandruff, atopic dermatitis, psoriasis, rosacea or acne.

Substances may up- or down-regulate the activity of the MAST4 gene at the nucleic acid and/or polypeptide level. As non-exhaustive representative examples, up-regulation may be achieved by administering substances which cause an increase in the transcription and/or translation of the MAST gene(s), or administering a nucleic acid molecule which directs the expression of all or part of a MAST gene product. For example, the inventors have identified binding sites for two transcription factors in the MAST4 gene which transcription factors may enhance the transcription of the MAST4 gene. Modulating the interaction between one or both of these transcription factors and the MAST4 gene may modulate the level of expression of the MAST4 gene.

For the avoidance of doubt, modulation of MAST gene activity may encompass delivery of additional MAST gene coding sequences so as to bring about a "gene dosing" effect by causing increased levels of expression of the MAST gene (especially a MAST4 gene) in the subject. Equally, the invention may encompass the direct application of a MAST polypeptide (especially a MAST4 polypeptide) to the skin of the subject to as to bring about a localised increase in concentration of the MAST polypeptide in or on the skin of the subject where up-regulation is required.

Down-regulation of MAST gene activity can be achieved at the polypeptide level by administering a compound which inhibits the activity or function of the MAST gene-expressed polypeptide. One class of such compounds are immunoglobulins and antigen-binding portions or fragments of immunoglobulin molecules. The immunoglobulin may be an antibody of any class (although IgG, IgA or IgM are generally preferred) which has binding activity for the MAST gene-expressed polypeptide. Alternatively the compound may be one of the many well-known portions or fragments of an immunoglobulin molecule which retains the ability to bind to the MAST gene-expressed polypeptide. Such include $F_{ab}$, $F(ab')_2$, single chain $F_v$ ($scF_v$), single domain antibodies (dAbs) and the like.

The immunoglobulin or immunoglobulin portion or fragment will preferably have a dissociation constant $K_D$ for the MAST polypeptide of $10^{-8}$ or less, more preferably $10^{-9}$ or less, and most preferably at least $10^{-10}$ or less. The $K_D$ will generally be in the range $10^{-8}$ to $10^{-11}$.

The immunoglobulin or immunoglobulin portion or fragment will preferably be relatively specific in its binding for the MAST polypeptide. The person skilled in the art recognises that an immunoglobulin being described as "specific" for a particular antigen relates to the fact that the antigen-binding site located within the variable domains of the light and heavy chains (defined as the "paratope") will bind more or less exclusively to the antigen which triggered the production of the antibody. This usually involves high affinity binding, resulting from a variety of cooperative molecular interactions. However, there are other regions of the antibody molecule which can be bound by other molecules, such as Fc receptors, complement proteins and various bacterial proteins, such as protein-A from *Staphylococcus aureus*. Moreover, as a relatively large protein, an antibody molecule is prone to all the non-specific binding interactions that can cause proteins in general to bind more or less avidly to surfaces with which they come into contact. These non-specific binding interactions are generally shared among all antibodies of the same class, regardless of their antigen specificity. Thus, an antibody will generally bind to its cognate antigen with an affinity that is orders of magnitude greater than the affinity with which it binds to most other molecules.

Equally the person skilled in the art will recognise that the term "immunoglobulin" does not necessarily indicate that a single molecular species is required. Rather, the term can encompass a heterogeneous mixture or population of molecules, and a "specific immunoglobulin" may refer to that portion of a mixture which is specific for the antigen in question.

Some MAST polypeptide-specific immunoglobulins are commercially available and include, for example, ab87734 (from AbCam, Cambridge UK), which is a rabbit polyclonal antibody which binds to an epitope between amino acids 1900 and 1905 of the human MAST4 polypeptide; ab196777, another rabbit polyclonal antibody which binds to human MAST4 polypeptide (available from AbCam; and also from Gene Tex GTX87899); PA5-36976 (from ThermoFisher), a rabbit polyclonal specific for human MAST4 polypeptide; and HPA000544 (Sigma), a rabbit polyclonal which binds to an epitope located in amino acid residues 1545-1652 of human MAST4 polypeptide.

Other molecules which can inhibit the activity of a MAST polypeptide, especially a MAST4 polypeptide, include small organic chemical compounds (e.g. with a relative molecular mass below 5,000, preferably below 4,000, and most preferably below 3,000).

Figure 2:
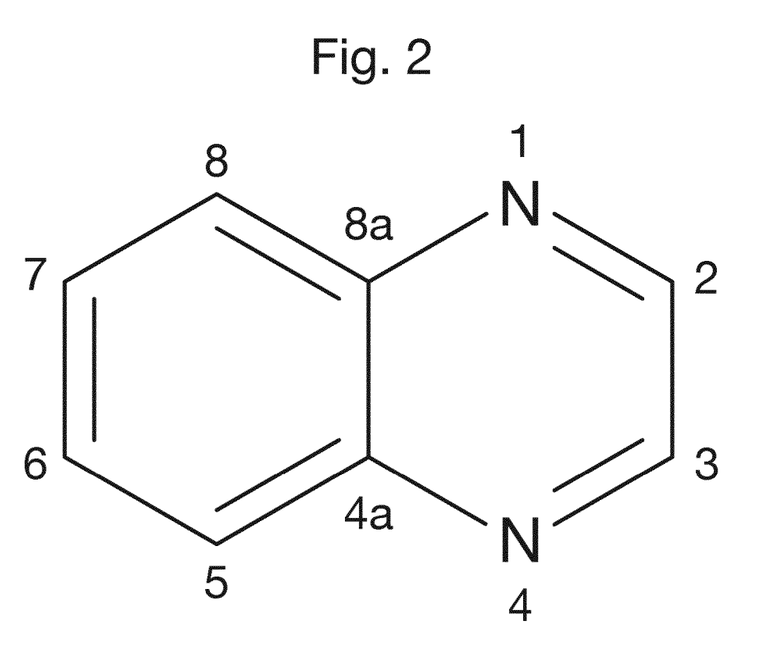
FIG. 2 shows the general chemical structure of quinoxaline and derivatives thereof.

In particular, a preferred small organic molecule inhibitor of MAST polypeptides comprises the class of quinoxalines and derivatives thereof. Quinoxaline and quinoxaline derivatives comprise a heterocyclic ring complex made up of a nitrogen atom at positions 1 & 4. The structure of quinoxaline is shown in FIG. 2. Quinoxaline and its derivatives have been reviewed by Pereira et al., 2014 (European Journal of Medicinal Chemistry 97, p 664-672) and by Tristan-Manzano et al., 2015 (Current Medicinal Chemistry 22, p 3075-3108). Quinoxaline derivatives are easy to synthesize (Porter et al., "Pyrazines and their benzo derivatives", Boulton & McKillop Eds. Compr. Heterocycl. Chem. Pergamon Press, Oxford 1984, 3; Sato et al., "Pyrazines and their benzo derivatives", Katritzky, Ramsden, Scriven & Taylor Eds. Compr. Heterocycl. Chem. III, Elsevier Oxford 2008, 8).

A number of quinoxaline derivatives have been shown to be potent inhibitors of MAST proteins (see Li et al., Biorganic & Medicinal Chemistry Letters 2013, 23, p 5217-5222).

Figure 3:
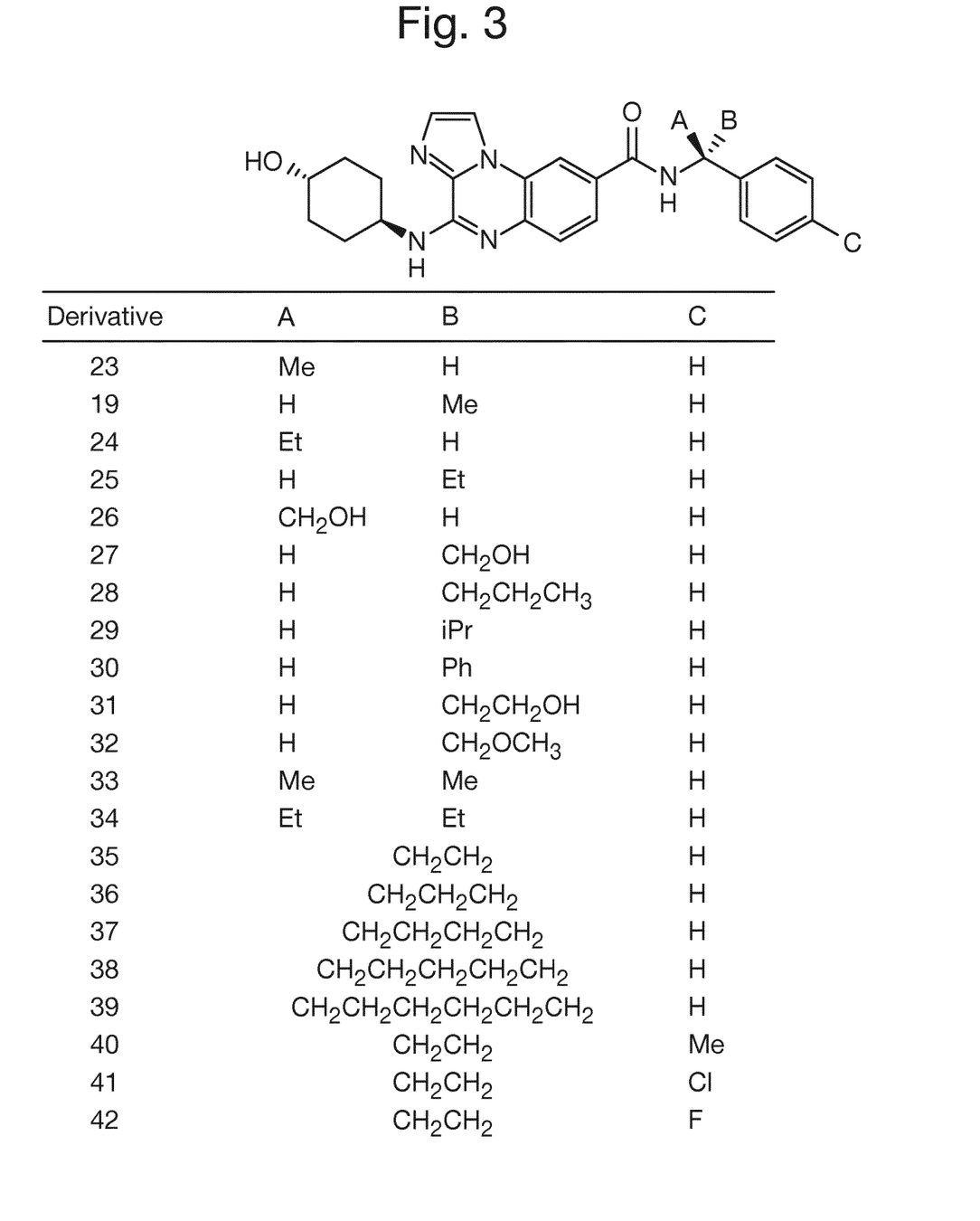
FIG. 3 illustrates the structure of certain quinoxaline derivatives which are preferred for use in the present invention.

Preferred quinoxaline derivatives for use in the present invention include imidazo quinoxalines. Li et al., (cited above) identified several quinoxaline derivatives which were both potent and relatively selective inhibitors of MAST polypeptide kinase activity. Accordingly, preferred quinoxaline derivatives for use in the present invention include the following: imidazo [1, 2-α]—quinoxalines, especially 4-chloro imidazo [1, 2-α] quinoxaline. Other preferred quinoxaline derivative inhibitors of MAST polypeptide kinase activity are illustrated in FIG. 3. The synthesis of these compounds is disclosed by Li et al (above).

The Hidden Markov Model library algorithm SUPERFAMILY (a database of structural and functional annotation for all proteins and genomes) locates the MAST4 PDZ domain starting at amino acid residue 1139 and ending at amino acid residue 1231 (supfam.org/SUPERFAMILY/cgi-bin/scop.cgi?ipid=SSES0156). Other algorithms (Gene 3D, Prosite, Smart and Pfam) identify the PDZ domain at MAST4 in the same region of the molecule (from about residue 1137 to 1231).

The crystal structure of the MAST4 PDZ domain has been solved and published (Elkins et al 2010 Protein Sci. 2010 April; 19(4):731-741.)

Alignment of the MAST family protein sequences shows that, whilst not identical, the PDZ domain is highly conserved between MAST protein family members.

Accordingly it is possible to design small peptides that specifically target the MAST4 PDZ domain which could disrupt interactions of MAST4 with its target proteins thereby modulating its function. Pull down studies (Valiente et al 2005 J. Biol. Chem. 289 (32) 28936-28943) support the potential to design selective MAST4 PDZ inhibitors since in these studies the MAST4 PDZ domain did not bind to PTEN whereas MAST2 and MAST3 PDZ domains did.

The physiological target proteins that the MAST4 PDZ domain binds to have not yet been determined, but analysis with String DB (string-db.org/cgi/), which uses text-mining, co-expression analysis and experimental data to predict protein/protein interactions identifies the following as putative functional partners for MAST4: GALNS, DNAJC6, TPTE2, TENC1, ARID4B, SPG21, PTEN, TNS3, SRL and TPTE. In addition an interaction between MAST4 and SMAD1 was reported by Colland et al following a Yeast 2-hybrid screen of SMAD protein interactions, (Colland et al 2004 Functional proteomics mapping of a human signaling pathway. Genome Res. 2004 July; 14(7):1324-32).

In view of the foregoing, immunoglobulins or antigen-binding fragments thereof which bind at or close to the kinase domain or the PDZ domain of the MAST4 protein should successfully inhibit its activity. Equally, given that the crystal structure of the MAST4 PDZ domain has been determined, it would be relatively straightforward for the person skilled in the art to devise a small molecule, such as a peptide, which could bind to the MAST protein PDZ domain or otherwise inhibit the interaction between the PDZ domain and its ligand.

27-hydroxycholesterol has also been shown to regulate MAST4 (see Nelson, Molecular and Cellular Endocrinology Volume 466, 5 May 2018, Pages 73-80).

Other molecules can inhibit MAST activity at the nucleic acid level (e.g. inhibit transcription and/or translation of the MAST genes, especially the MAST 4 gene). As an example, short interfering RNA (siRNA) molecules, typically about 20-30 bp with one or two nucleotide overhangs at each end, can readily be prepared, since the sequence of the MAST genes is known (e.g. the MAST4 gene is located on the forward strand of chromosome 5 and comprises nucleotides 66,596,361 to 37,169,595 (human genome build GRCh 38: CM 000667.2)). The MAST4 gene is predicted to encode 21 transcripts, many of which have been experimentally validated. Transcript: MAST4-001 ENST00000403625.6 encodes the longest polypeptide (2623 amino acids) with 29 exons and is currently annotated with 40 domains and features, and maps to 85 oligo probes.

Details of the other MAST genes are as follows:

MAST1 gene location: Chromosome 19: 12,833,951-12, 874,951 forward strand (Human genome build GRCh38: CM000681.2). MAST1 synonyms: SAST170, SAST, KIAA0973.

In the MAST1 gene product, a protein kinase domain is located around amino acid residues 372-647 and the PDZ domain around amino acid residues 958-1057.

MAST2 gene location: Chromosome 1: 45,786,987-46, 036,124 forward strand (Human genome build GRCh38: CM000663.2). MAST2 synonyms: KIAA0807, GN MAST205, KIAA0807, MTSSK, MAST205.

In the MAST2 protein, a protein kinase domains located in the region of amino acid residues 510-860, more especially residues 512-785.

MAST3 gene location: Chromosome 19: 18,097,793-18, 151,692 forward strand (Human genome build GRCh38: CM000681.2). MAST3 synonyms: KIAA0561.

In the MAST3 protein, a protein kinase domain is located around residues 365-719, and more especially at residues 367-640.

Increasing activity of the MAST genes, especially the MAST4 gene, at the nucleic acid level could be accomplished by administering a transcription factor which increases the transcription of the MAST gene. Transcription factors known, or likely, to enhance transcription of the MAST genes include CCAAT/enhancer binding protein (abbreviated as CEBP beta), since the inventors have found that the MAST4 gene includes a CEBP beta transcription factor binding site. Alternatively, substances which modulate the binding of CEBP beta to MAST4 may up- or down-regulate the level of transcription of MAST4.

CEBP beta is available from commercial sources, either as a purified protein or as a nucleic acid sequence encoding the polypeptide, from e.g. Genscript, Cloud-Clone and Ori-Gene. Equally, CEBP beta-specific antibodies are available from commercial sources such as AbCam. Known agonist proteins/agonist genes of CEBP beta include INS, EGR2, CDK2, GSK3B, MAPK3, ABL1, ABL2 and MAPK1. Conversely, known antagonist gene/proteins of CEBP beta include: GATA3, SOX9, GATA2, SMAD3, and SMAD4.

Accordingly, there are a variety of substances which are commercially available, or readily produced, which could be used to up- or down-regulate the expression of CEBP beta and/or to inhibit the interaction of the protein with the MAST4 gene. In particular, antibodies (or antigen-binding portions of antibodies) specific for CEBP beta could inhibit binding of the protein of the MAST4 sequence.

The inventors have also identified (by inspection of the Open Regulatory Annotation Database, also known as "ORegAnno") that there is another predicted transcription factor binding site in the region of the MAST4 gene identified as being of special relevance. This transcription factor is SMARCA4 (OReg ID 1274278), also known as BRG1. SMARCA4 is a "chromatin remodeller" and promotes expression of genes involved in epidermal barrier repair (Botchkarev, Journal of Invest. Dermatol. Symposium 2015, 17 [18-19]), as well as controlling hair follicle tissue remodeling (Xiong et al., Developmental Cell 2013, 25, 169-181). Thus the presence of a binding site for this transcription factor supports a role for MAST4 in maintaining epidermal integrity, which one can predict will be associated with susceptibility to skin inflammation.

Thus, as an alternative to, or in addition to, modulating the interaction between CEBP beta and MAST4, one can modulate the expression of MAST4 by regulating the interaction between SMARCA4 and the MAST gene. There are commercial sources of the SMARCA4 protein/nucleic acid, and also SMARCA4-specific antibodies, as for CEBP beta. Known agonists of SMARCA4 include MYOD1 and MYOG. Known antagonists include PFI3, which is a potent and selective inhibitor of SMARCA4 with a Kd value of 89 nM (Vangamudi et al., Cancer Res. 2015, pii:canres. 3798.2015).

In a second aspect, the invention provides an in vitro assay method to identify substances having potential efficacy for treating and/or preventing an inflammatory skin condition in a human subject, the assay method comprising the steps of: contacting, separately, a plurality of candidate substances with a MAST4 gene or MAST4 gene product; and identifying those candidate substances which have a down-regulatory effect on the activity of the MAST4 gene or MAST4 gene product.

The candidate substances may have a direct or an indirect modulatory effect on the activity of the MAST4 gene or MAST4 gene product. In the context of the present invention, the modulatory effect is down-regulation. In an alternative, the modulatory effect may be up-regulation.

The assay may include an in vitro expression system to express the MAST gene. Generally suitable in vitro expression systems are commercially available and known to those skilled in the art.

The amount of MAST4 gene or MAST4 gene product activity may be directly measured, or inferred, by any suitable method. For example, there are numerous techniques for assaying the level of expression of a gene, and these include, for instance, use of a linked marker or reporter gene, such as luciferase, fluorescent protein (e.g. GFP), or chloramphenicol acetyl transferase (CAT) assays.

Methods of assaying MAST polypeptide amount or activity include methods of assaying the kinase activity of the MAST polypeptide. Generally suitable kinase assay techniques which can be of use in this aspect of the invention include:
(a) Measuring production of ADP from ATP in a system expressing or containing the target kinase (eg MAST4). This can be assessed through a range of direct and indirect reporters such as radioisotope labels, antibody-coupled fluorescence or luminescence eg in the Promega ADP-Glo™ Kinase AssayADP-Glo™ Kinase AssayADP-Glo™ assay where the ADP produced by the kinase reaction is converted into light by a Luciferase;
(b) Detection of phospho-serine in peptide substrates following reaction with expressed kinase target. The detection may use antibodies coupled to a reporter system such as β-galactosidase in GE lifesciences Discover-RX assay or antibody coupled to a fluorescence reporter by TR-FRET as in the Thermofisher LanthaScreen platform);
(c) Using modified substrate peptides specific to the target kinase coupled to a reporter system; and
(d) Cellular pathway analysis for example the Thermofisher CellSenor® cell lines which are stably engineered to express beta-lactamase reporter under the control of pathway-specific response elements.

A comprehensive review of kinase assay approaches is summarized in table 1 of Assay Development for Protein Kinase Enzymes by J. Fraser Glickman, M.S.P.H., PhD. Rockefeller University, New York, N.Y., 10065

The candidate substances may conveniently be tested in parallel with a positive control, using a compound known to be active in modulating the activity of a MAST4 gene or a MAST4 gene product (e.g. a MAST polypeptide-specific immunoglobulin; or a small molecule inhibitor such as 4-chloroimidazo [1, 2-α] quinoxaline): preferably candidate substances will be at least as effective as the positive control in modulating the activity of the MAST gene or MAST gene product, more preferably the candidate compounds will be 10%, 20%, 30%, 40%, 50%, 60%, 70%, 80%, 90% or even up to 100% more effective (at an equivalent molar concentration) than the positive control at modulating the activity of the MAST gene or MAST gene product.

In a third aspect the invention provides for use of a MAST4 gene product, or a nucleic acid molecule expressing a MAST4 gene product, in a screening assay to identify substances which modulate the activity of a MAST4 gene product or nucleic acid molecule expressing a MAST4 gene product, and thus identify substances which may be useful to treat and/or prevent an inflammatory skin condition in a human subject. In the context of the present invention, the modulatory effect is down-regulation. In an alternative, the modulatory effect may be up-regulation.

The invention may also provide a method of making a prophylactic and/or therapeutic formulation for prevention and/or treatment, as appropriate, of an inflammatory skin condition in a human subject, the method comprising mixing an active substances effective in modulating the activity of a MAST4 gene or a MAST4 gene product with a suitable diluent, excipient or carrier, the active substance being identified by the assay method of the second aspect of the invention.

The active substance of the various aspects of the invention may be a complex mixture (e.g. a natural plant extract or the like), or may be a substantially purified or isolated compound. Further, the active substance may comprise a single active compound, or may comprise a plurality of active compounds, which may act additively or, more preferably, synergistically in modulating the activity of the MAST gene or gene product.

Preferably the formulation will comprise one or more additional active compounds, and these may conveniently comprise known anti-inflammatory compounds, especially anti-inflammatory compounds which are known and approved for topical application. Such compounds include corticosteroids, as described below.

The person skilled in the art can establish a suitable dose of the active compound or compounds, and hence a suitable concentration in the formulation, by means of routine trial and error, and such does not form an inventive part of the present invention.

Delivery Mechanisms

The mechanism for delivering an active agent, to up- or down-regulate the activity of a MAST gene, or transcription or translation product thereof, can be any mechanism which delivers an effective dose of active agent whilst avoiding significant unacceptable side effects. For present purposes, an effective dose of active agent is a dose which produces a discernible improvement in the condition of an inflammatory skin disease (especially SD) for a therapeutic effect, or which prevents the development of an inflammatory skin disease (especially SD), for a prophylactic effect.

The active agent may be delivered orally or by injection (preferably subcutaneous, or less preferably, intramuscular). However, most preferably the active agent will be delivered by topical application to the skin of a subject, which may conveniently be a region of the skin affected by an inflammatory skin disease when the subject has an active condition, and/or may be a portion of the skin which is susceptible to an inflammatory skin disease if the subject has no symptoms at the time of applying the formulation. For example, where the disease is SD, the active agent may be topically applied to one or more of the scalp, face or chest, but may equally be applied to other areas of the skin if those other areas are also affected.

If the active agent is applied topically, it may be desirable for the formulation in which the active agent is present to further incorporate a penetration enhancer.

Examples of chemical penetration enhancers include a percutaneous absorption accelerator such as isopropyl myristate, a surfactant, alcohol or the like, including C6-C20 fatty acids, fatty alcohols, fatty acid esters, amides or ethers, aromatic organic acids, aromatic alcohols, aromatic fatty acid esters or ethers (these may be saturated or unsaturated, and may be cyclic, straight or branched), especially lactic acid esters, acetic acid esters, monoterpene compounds, sesquiterpene compounds, azone, azone derivatives, pirotiodecane, glycerol fatty acid esters, propylene glycol fatty acid esters, sorbitan fatty acid esters (Span type), polysorbates (Tween® type), polyethylene glycol fatty acid esters, polyoxyethylene hardened castor oils (HCO type), polyoxyethylene alkyl ethers, sucrose fatty acid esters, plant oils and the like. Particular examples include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, diethyl sebacate, lauric acid diethanolamide, triethanolamine, isopropyl myristate, myristyl myristate, octyldecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerol monocaprylate, glycerol monocaprate, glycerol monolaurate, glycerol monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, pyrothiodecane. Percutaneous absorption may also be enhanced using hydrogel vehicles, microemulsions, nanoparticles or solid lipid nanoparticles.

Mechanisms of delivery include the following: direct application to the skin of a liquid (such as a shampoo and/or conditioner), cream, gel, lotion, paste, patch or the like containing the active agent; application to the skin of a formulation comprising the active agent incorporated into liposomes, ethosomes, transfersomes or similar synthetic vesicle comprising a lipid bilayer; application to the skin of a formulation comprising the active agent loaded on, incorporated into or attached to nanoparticles. Methods of preparing liposomes, ethosomes, transfersomes etc. are well known to those skilled in the art. A transfersome is a special sort of liposome which is highly deformable as a consequence of the inclusion of a surfactant and/or other amphiphilic molecule in the bilipid layer. An ethosome is, in essence, a lipsome comprising a relatively large amount (typically 20-45% w/w) of ethanol. For present purposes, the term "lipid bilayer" includes bilayers formed from or comprising modified lipids, such as phospholipids, glycolipids, phosphoglycolipids.

The mechanisms described above may optionally be combined with the use of a chemical penetration enhancer and/or a physical penetration enhancer.

Physical penetration enhancement may include one or more of the following: iontophoresis, electroporation, ultrasound or the use of microneedles or other dermabrasion techniques, which may be used prior to, and/or simultaneous with, and/or subsequent to, application of the formulation to the skin of the subject.

The topical delivery of siRNA has been achieved using viral or nonviral methods, and the combination of non-viral methods with an active permeation method such as iontophoresis, sonophoresis or microneedles for the treatment of skin disorders.

Zheng et al 2012 (pnas.org/content/109/30/11975.abstract) describe using sperical nucleic acid nanoparticle conjugates ("SNA-NCs", gold cores surrounded by a dense shell of highly oriented, covalently immobilized siRNA) which freely penetrated almost 100% of keratinocytes in vitro, mouse skin, and human epidermis within hours after application. Significantly, these structures can be delivered in a commercial moisturizer or phosphate-buffered saline, and do not require barrier disruption or transfection agents, such as liposomes, peptides, or viruses. In addition, Chong et al report gene silencing following siRNA delivery to skin via coated steel microneedles (Chong et al., 2013. *Journal of Controlled Release* 166(3), pp. 211-219).

Furthermore, recent work with delivery of Crispr/Cas9 components suggests that this may also be a possible avenue for delivery of relevant mucleic acid molecules which may directly or indirectly modulate the activity of a MAST gene.

Formulations

The practice of the invention will typically involve administering one or more active agents (i.e. active to up- or down-regulate the activity of a MAST gene or transcription or translation product of a MAST gene) in combination with a bulking agent, diluent, excipient, carrier or the like.

Suitable diluents, excipients and carriers are known to those skilled in the art and include, inter alia, aqueous solutions (such as saline, phosphate-buffered saline or other buffer preparations), emulsions, oils etc.

The precise composition of the formulation will depend, inter alia, on its method of application. Conveniently the formulation will be adapted and configured for topical application to the skin of a human subject and may take the form of, inter alia, a cream, lotion, paste, gel or patch, especially a self-adhesive and/or occlusive patch. In some embodiments the formulation may be that of a shampoo and/or conditioner, which may be formulated to be rinsed off or left on the hair. Shampoo and/or conditioner formulations are known to those skilled in the art and typically include one or more of the following: water, detergent, surfactant, thickening agent, a betaine, humectant, perfume or fragrance and dye or pigment.

It is generally preferred that the formulation may additionally comprise one or more known, conventional anti-inflammatory agents, especially an anti-inflammatory agent known and approved for topical use. Most such compounds are corticosteroids. Non-corticosteroidal anti-inflammatory agents include coal tar preparations. Anti-inflammatory corticosteroids include: betamethasone dipropionate, clobetasol propionate, diflorasone diacetate, halobetasol propionate, amcinonide, desoximetasone, fluocinonide, halcinonide, mometasone furoate, fluticasone propionate, triamcinolone acetonide, fluocinolone acetonide, flurandrenolide, betamethasone valerate, desonide, hydrocortisone, hydrocortisone butyrate, hydrocortisone valerate, hydrocortisone acetate, and pramoxine hydrochloride.

The invention will now be further described by way of illustrative example and with reference to the accompanying drawings, in which.

EXAMPLES

Example 1—Candidate Gene Association Study (CGAS) and Genome-Wide Association Study (GWAS)

In this example, the inventors conducted a candidate gene association study (CGAS) to investigate whether genetic variants previously associated with AD and PSO are also associated with an increased risk for SD, and conducted the first genome-wide association study (GWAS) to identify novel genetic variants associated with SD.

Methods

Study Population.

The Rotterdam Study (RS) is an ongoing prospective cohort study of chronic diseases, including skin diseases, in the elderly. A detailed description of the study can be found elsewhere (Hofman et al. The Rotterdam Study: 2016 objectives and design update. Eur J Epidemiol. 2015; 30(8):661-708). In brief, the Rotterdam Study consists of a major cohort (RS-I) and two extensions (RS-II and RS-III). RS-I started in 1990 and initially included 7,983 participants living in the Ommoord district in Rotterdam, The Netherlands. RS-II started in 2000 and includes 3,011 participants. RS-III is a further extension of the cohort, started in 2006, and includes 3,932 participants. In total, the Rotterdam Study consists of 14,926 subjects aged 45 years or over. The cohort consists predominantly (90%) of participants of North-European ancestry.

The Rotterdam Study was approved by the Medical Ethics Committee of the Erasmus MC and by the Ministry of Health, Welfare and Sport of the Netherlands. All participants provided written informed consent to participate in the study and to obtain information from their treating physicians.

Case Definition

A total of 4,454 participants from the Rotterdam Study with available genotype data underwent a full body skin examination (FBSE) by trained physicians to assess whether a participant had SD. The clinical diagnosis was based on the presence of greasy scaling, erythema and a characteristic distribution of the scalp, face and/or chest. Participants who did not have any sign of active disease and without a history of ketoconazole use ($\geq 3$ prescriptions using pharmacy linkage data) were included as controls.

Selection of Candidate Loci

PubMed was searched for well-powered European GWAS that showed an association between single nucleotide polymorphisms (SNPs) and PSO or AD. The inventors selected SNPs with a significance level of $<5.0 \times 10^{-8}$. The reported (lead) SNP was used for the SNP-based association analysis and was used to select a locus region for a gene-based candidate gene association study.

For lead SNPs located within a gene, a 30 kb region (plus 15 kb downstream and 15 kb upstream of the gene) was added to include regulatory elements close to the gene. If the lead SNP was intergenic and located more than 15 kb away from a gene, the inventors also added 15 kb downstream and 15 kb upstream from the base-pair position of the lead SNP. The NCBI Variation Viewer (http://www.ncbi.nlm.nih.gov/variation/view/) with build CRCh37 was used to retrieve the gene genomic coordinates. These coordinates were used to retrieve SNPs in the corresponding regions of the Rotterdam Study cohorts.

Genotyping and Imputation

DNA extraction from whole blood genotyping, imputation and quality control were carried out following standard protocols, as described earlier (Hofman et al. Eur J Epidemiol. 2015; 30(8):661-708; Verkouteren et al., J Invest Dermatol. 2015; 135(8):2135-8). The Illumina Infinium II HumanHap550 BeadChips were used to genotype the RS-I and RS-II cohorts while Illumina Human610-Quad BeadChips were used to genotype the RS-III cohort.

Quality control on the single-nucleotide polymorphism (SNP) included removing SNPs with Hardy-Weinberg equilibrium deviations (p-value$<5 \times 10^{-6}$), genotype call rate <97%, gender mismatch and a high mean autosomal heterozygosity. First-degree relatives were removed and SNPs were filtered out if they had a minor allele frequency of less than 1% or an imputation quality (Rsq) of less than 0.3.

Candidate Gene Study

The candidate gene association studies (CGAS) were performed in two steps. First, a SNP-based association study of previously associated PSO and AD SNPs and second, a gene-based association analysis was conducted to screen for additional variants within the regions of interest.

The SNP-based CGAS of SD cases and controls were performed using the imputed dosage data of each Rotterdam Study cohort using a logistic regression with an additive model. The output per SNP for each Rotterdam Study cohort was meta-analyzed using p-values derived from a likelihood ratio test as summary statistics (Willer et al., METAL: fast and efficient meta-analysis of genomewide association scans. Bioinformatics. 2010; 26(17):2190-1; Aulchenko et al., ProbABEL package for genome-wide association analysis of imputed data. BMC Bioinformatics. 2010; 11:134).

Best-guessed genotypes were used for the gene-based CGAS. The genotypes of the three Rotterdam Study cohorts were estimated from the imputed dosage data using the GCTA software with default parameters (Yang et al., Am J Hum Genet. 2011; 88(1):76-82).

The gene-based logistic regression was conducted using the set-based test implemented in PLINK v.190 (paramters: p-value=0.05, maximum number of SNPs=15, $r^2$=0.5, permutations=10000) (Purcell et al. PLINK: a tool set for whole-genome association and population-based linkage analyses. Am J Hum Genet. 2007; 81(3):559-75). Both SNP-based and gene-based associations were adjusted for age, sex and four principal components (PCs).

Genome-Wide Association Study

A GWAS of SD cases and controls was performed using the imputed dosage data of each Rotterdam Study cohort using a logistic regression with an additive model. The model was adjusted for age, sex and four PCs. The GWAS analyses were implemented in the ProbABEL package (Aulchenko et al., cited above). The inflation factor λ was estimated close to 1.0 and was not further considered.

Next, the GWAS summary statistics per Rotterdam Study cohort were meta-analyzed using p-values derived from a likelihood ratio test. The meta-analysis was carried-out using METAL (Willer et al., cited previously). The threshold for the p-value of genome wide significance was set at a p-value≤$5 \times 10^{-8}$.

Results

Study Population 4,050 of the 4,454 participants were included for the CGAS and GWAS of SD. Of these, 609 (15%) were diagnosed during a FBSE by a research physician as having SD. Males were more likely to have SD than were females (60.4% of cases vs 41.8% of controls were males; p-value<0.001) and SD patients were older compared to those without SD (68.94 vs 67.97, p-value: 0.018). SD cases were more likely to have the diagnosis of psoriasis than controls (4.8% vs 3.0%; p=0.035).

Candidate Genes Approach

The CGAS did not yield any significant locus for SD after correcting for multiple testing.

Genome Wide Association Study

To discover new loci for SD, the inventors performed a GWAS on SD cases against controls and over 7 million loci and found two genome-wide significant associations (Table 1). The most significant SNP was rs58331610 that mapped to an intronic region of the MAST4 gene at chromosome 5 (p-value: $1.75 \times 10^{-8}$). The second hit was the rs16944244 SNP that mapped to an intergenic region at chromosome 17p12, between the genes PIRT and SHISA6 (p-value: $2.10 \times 10^{-8}$). In addition, 68 SNPs in seven different loci were found to be significantly associated with SD with suggestive genome-wide associations (p-value<$5 \times 10^{-6}$) in this relatively small sample of SD patients. Several SNPs mapped to protein-coding genes including GRM3 (rs6978155, $5.24 \times 10^{-7}$), KIAA1324L (rs73382367, $6.51 \times 10^{-7}$) and SENP2 (rs13081203, $3.64 \times 10^{-6}$), while others were intergenic. None of these loci have been previously associated with PSO or AD.

TABLE 1

| Gene | SNP | Chr | Location | Allele | | Freq | Pvalue |
| --- | --- | --- | --- | --- | --- | --- | --- |
| MAST4 | rs58331610 | 5 | 66020457 | a | g | 0.8615 | $1.75 \times 10^{-8}$* |
| Intergenic | rs16944244 | 17 | 11026693 | c | g | 0.9796 | $2.10 \times 10^{-8}$* |
| Intergenic | rs78160483 | 17 | 11026297 | t | g | 0.9818 | $8.38 \times 10^{-8}$ |
| Intergenic | rs16944241 | 17 | 11026414 | a | g | 0.9818 | $8.38 \times 10^{-8}$ |
| Intergenic | rs6546997 | 2 | 75658780 | t | c | 0.1894 | $9.53 \times 10^{-8}$ |
| Intergenic | rs8075550 | 17 | 11027059 | a | g | 0.9594 | $1.04 \times 10^{-7}$ |
| Intergenic | rs11870758 | 17 | 11015902 | a | t | 0.9722 | $1.21 \times 10^{-7}$ |
| MAST4 | rs12188593 | 5 | 66030069 | t | c | 0.1359 | $1.27 \times 10^{-7}$ |
| Intergenic | rs182131544 | 17 | 11023964 | a | g | 0.9788 | $1.32 \times 10^{-7}$ |
| Intergenic | rs111448323 | 17 | 11022815 | a | g | 0.9786 | $1.50 \times 10^{-7}$ |
| Intergenic | rs4791451 | 17 | 11027570 | c | g | 0.9808 | $1.54 \times 10^{-7}$ |
| Intergenic | rs77699632 | 17 | 11020937 | a | t | 0.0214 | $1.73 \times 10^{-7}$ |
| Intergenic | rs111341744 | 17 | 11021220 | a | g | 0.9784 | $1.79 \times 10^{-7}$ |
| Intergenic | rs75205996 | 17 | 11021311 | t | c | 0.9784 | $1.79 \times 10^{-7}$ |
| Intergenic | rs58692658 | 17 | 11019423 | t | c | 0.022 | $2.32 \times 10^{-7}$ |
| Intergenic | rs77592872 | 17 | 11018841 | a | t | 0.9781 | $2.34 \times 10^{-7}$ |
| Intergenic | rs138424360 | 17 | 11018089 | a | g | 0.0219 | $2.37 \times 10^{-7}$ |
| Intergenic | rs80298958 | 17 | 11016351 | c | g | 0.9784 | $3.39 \times 10^{-7}$ |
| Intergenic | rs76730906 | 17 | 11019589 | t | g | 0.9754 | $3.85 \times 10^{-7}$ |
| GRM3 | rs6978155 | 7 | 86477894 | a | t | 0.0543 | $5.24 \times 10^{-7}$ |
| GRM3 | rs6957842 | 7 | 86477870 | a | t | 0.9457 | $5.28 \times 10^{-7}$ |
| GRM3 | 7:86475369:I | 7 | 86475369 | d | i | 0.9459 | $5.63 \times 10^{-7}$ |
| GRM3 | rs6960053 | 7 | 86473063 | a | g | 0.0541 | $5.68 \times 10^{-7}$ |
| GRM3 | rs6974507 | 7 | 86472032 | t | g | 0.9459 | $5.75 \times 10^{-7}$ |
| GRM3 | rs7801589 | 7 | 86470943 | t | c | 0.9459 | $5.76 \times 10^{-7}$ |
| GRM3 | rs6465087 | 7 | 86470488 | t | c | 0.9459 | $5.78 \times 10^{-7}$ |
| GRM3 | rs6954573 | 7 | 86472161 | a | t | 0.9455 | $5.86 \times 10^{-7}$ |
| KIAA1324L | rs73382367 | 7 | 86525065 | a | g | 0.9436 | $6.51 \times 10^{-7}$ |
| KIAA1324L | rs6465089 | 7 | 86564795 | t | c | 0.0563 | $7.17 \times 10^{-7}$ |
| GRM3 | 7:86478749:I | 7 | 86478749 | d | i | 0.9453 | $7.44 \times 10^{-7}$ |
| GRM3 | rs6947778 | 7 | 86476124 | c | g | 0.0545 | $8.11 \times 10^{-7}$ |
| GRM3 | rs6967992 | 7 | 86476311 | t | c | 0.9455 | $8.11 \times 10^{-7}$ |
| GRM3 | rs6955565 | 7 | 86472484 | a | g | 0.0545 | $8.12 \times 10^{-7}$ |
| GRM3 | rs6955452 | 7 | 86472584 | c | g | 0.9455 | $8.15 \times 10^{-7}$ |
| GRM3 | rs6955917 | 7 | 86472763 | a | g | 0.0545 | $8.15 \times 10^{-7}$ |
| KIAA1324L | rs6958716 | 7 | 86594383 | t | c | 0.943 | $1.18 \times 10^{-6}$ |

*statistically significant

Discussion

In this study the inventors did not find statistically significant associations between previously associated PSO/AD SNPs and SD. However in the GWAS for SD, two SNPs with genome-wide significant associations were observed. In addition, genome-wide suggestive associations were found in other genes that may be relevant to the SD pathogenesis that need to be confirmed in other cohorts.

In the pilot GWAS for SD, several SNPs were significantly associated (p-value≤$5.0×10^{-8}$) with SD, including variants located at the MAST4 gene. MAST4 belongs to the protein kinase (PK) group, which plays a critical role in intracellular signal transmission cascades. The precise function of MAST4 is unknown, but the gene is expressed in different skin cells (Garza et al. J Clin Invest. 2011; 121(2): 613-22). Only 12 MB upstream of MAST4 lies the gene CD180, which directly interacts with the TLR4 signaling complex (Divanovic et al. Nat Immunol. 2005; 6(6):571-8). TLR4 plays an important role in the innate immunity of the skin. Expression studies have shown a disturbance in of expression of TLR4 in AD, PSO and contact dermatitis skin and a decreased expression of TLR4 is also found in treatment of SD with lithium gluconate (Elewa et al., J Dermatol. 2015; 52(5):467-76; Ballenger et al., Arch Dermatol Res. 2008; 300(5): 215-23). MAST3, a paralog of MAST4, is also known to influence TLR4 (Labbe et al. Genes Immun. 2008; 9(7):602-12).

The MAST4 gene has not previously been associated with any skin condition, such as PSO or AD.

Figure 1:
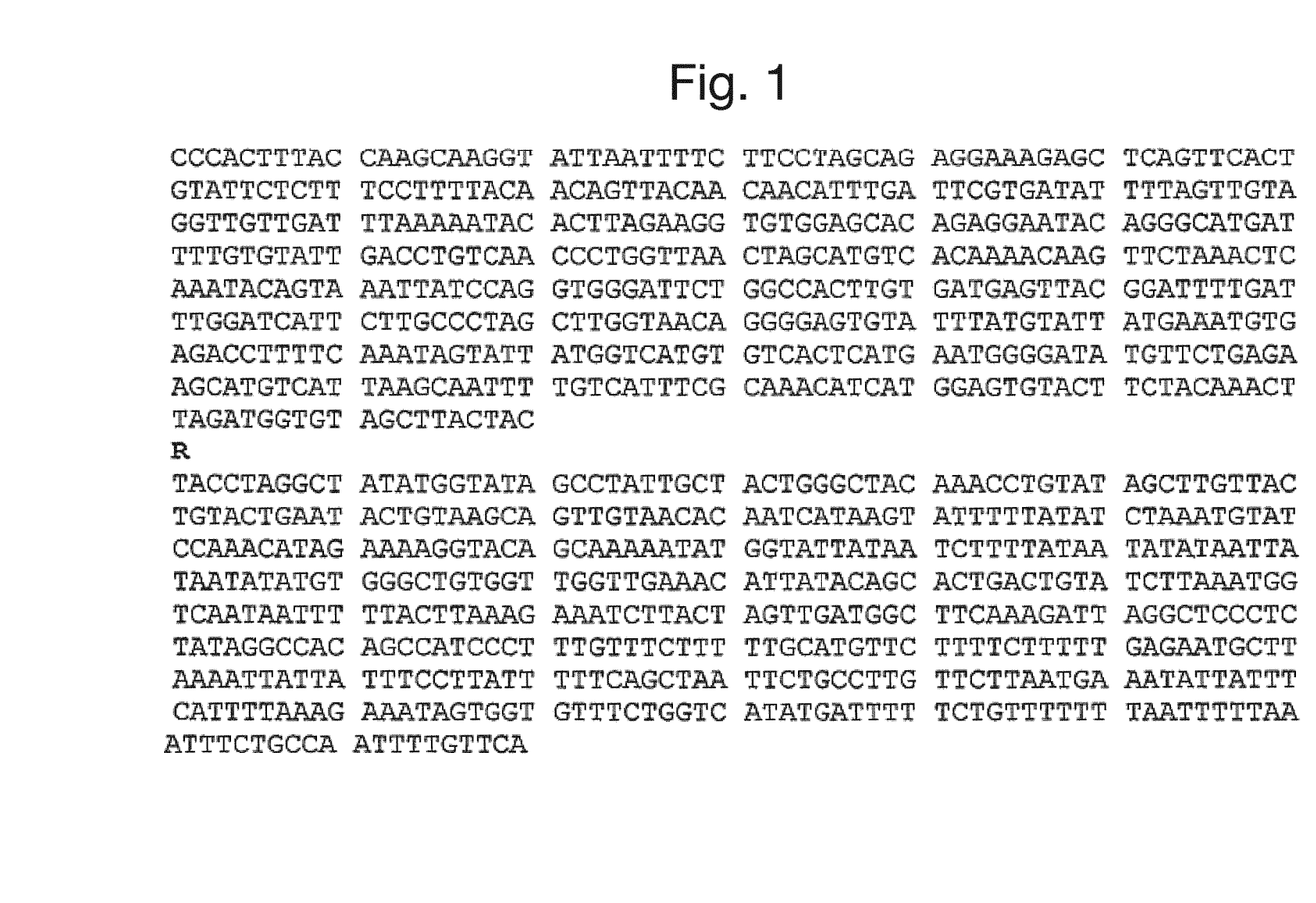
FIG. 1 shows SEQ ID NO: 1 setting forth the nucleotide sequence of part of the human MAST4 gene around a single nucleotide polymorphism identified by the inventors as associated with susceptibility to seborrheic dermatitis.

The SNP rs58331610 maps to a 9.6kb region of chromosome 5 in the first intron of the MAST4 gene. The genomic DNA nucleotide sequence immediately around the SNP is set forth in SEQ ID NO: 1 and is shown in FIG. 1. In that Figure, the location of the polymorphism is indicated by R (purine, i.e. A or G).

At time of writing, the most recent human genome assembly (GRCh 38/hg 38) provides the co-ordinates for SEQ ID NO: 1, shown in FIG. 1, as: chr5:66,724,129 to 66,725,129 (1001 bp). This region of the genome is located within the MAST4 gene, intron 1 (which has co-ordinates 66,597,019 to 66,759,708).

The frequency of the G allele in the Rotterdam Study group (which is largely of European Caucasian ancestry) is 0.139. According to the findings of the Genome Wide Association Study the G allele is associated with 'protection' from developing seborrheic dermatitis.

Interestingly, the data from the 1000 genome project shows that the frequency of this protective rs58331610 'G allele' varies substantially between different ancestral groups around the globe, ranging from <10% in some African groups up to 50% in some East Asian and Central and South American ancestral populations.

The SNP is strongly associated with SD, so it is possible that levels of expression of the MAST4 gene are associated with a predisposition to developing the condition. It follows that modulating the activity of the MAST4 gene, either up or down, may have a beneficial effect on prevention and/or treatment of the disease.

Not only that, but there are three other MAST genes known in humans (MAST 1, 2 and 3), all of which are expressed in the skin. It is possible that up- or down-regulation of one or more of MAST 1-3 may also have a beneficial effect on prevention and/or treatment of SD. However, MAST4 appears to be the MAST gene which is most highly expressed in human skin, and is therefore the prime candidate for prophylactic and/or therapeutic intervention in SD.

Using the MAPPER tool (genome.ufl.edu/mapper), the inventors found evidence that the rs58331610 SNP is present within a predicted C/EBP β transcription factor binding site.

Activity of C/EBP β is important in the regulation of genes involved in immune and inflammatory responses. C/EBP-β transcription factor regulates IL-17 responsive genes and is expressed preferentially in differentiated keratinocytes. Expression of C/EBPβ is up-regulated in psoriatic compared to healthy skin. C/EBP-β binding sites are particularly found in regulatory sequences of genes that are associated with the inflammatory response (europepmc.org/backend/ptpmcrender.fcgi?accid=PMC4324884&blobtype=pdf). CEBPβ was first identified on the basis of its ability to regulate gene transcription in response to IL-1 and IL-6. (ncbi.nlm.nih.gov/pmc/articles/PMC1222736/pdf/12006103.pdf).

Alternative names include NF-IL6, TCF5, IL-6DBP, LAP, CRP2, NF-M, AGP/EBP, ApC/EBP.

Accordingly, one hypothesis is that genetic variation at the SNP locus could affect the C/EBPβ binding site and alter the binding affinity for the transcription factor and hence modulate transcription and expression of the MAST gene.

Example 2—Demonstration that MAST4 Kinase is Required for Inflammatory Response to Microbial Challenge and that Inhibition of MAST4 Kinase can Reduce Inflammatory Response in Normal Human Epidermal Keratinocytes Method:

Normal Human Epidermal Keratinocytes were seeded at 40,000 cells per well in 24 well plates and grown for 16 hours in media (EpiLife® medium MEP1500CA)+HKGS supplement (S-001-5) at 37° C., 5% $CO_2$. The cells were transfected using RNAiMAX with 20 nM of either a MAST4 target specific stealth siRNA (Thermofisher HSS180104) or a medium GC specific control siRNA. After 48 hours the medium was removed and cells were challenged with 10 μg/ml peptidoglycan from *Staphylococcus aureus* (Sigma 77140) for 24 hours. The medium was harvested from the cells and total RNA was extracted from each cell sample using Qiagen.

RNeasy mini kit and quantitated on a NanoDrop. MAST4 gene expression was measured using standard gene expression analysis conditions and TaqMan® expression assay Hs00389519_m1. Duplicate 100 μl samples from each experimental well were analysed for IL8 using R&D systems IL8 duo-set ELISA.

Table 2 below shows the relative quantitation (RQ) of MAST4 gene expression in the cell samples compared to vehicle control and normalized to "housekeeper" (Actin) gene expression. The MAST4 siRNA knockdown successfully reduced MAST4 transcript levels by >80%.

Peptidoglycan challenge induced MAST4 transcript expression, increasing it by >25% in the cells transfected with control siRNA. This demonstrates that MAST4 gene expression is induced by peptidoglycan, which is a bacterial cell wall component, supporting a role for MAST4 in epidermal keratinocyte inflammatory immune response (Wang et al 2001 Infect. Immun. 69(4), 2270-2276). Peptidoglycan is known as a toll-like receptor 2 (TLR2) activator (Dziarski and Gupta 2005 Infect. Immun. 73(8), 5212-5216) and therefore this data supports a role for MAST4 in TLR2 mediated signaling in Normal Human Epidermal Keratinocytes.

TABLE 2

| siRNA | Treatment | Relative Quantitation of MAST4 expression | IL-8 (pg/ml) | IL-8 induction by peptidoglycan (pg/ml) |
|---|---|---|---|---|
| Control | Vehicle | 1 | 26.73 +/− 9.33 | NA |
| MAST4 | Vehicle | 0.166 | 32.94 +/− 10.96 | NA |
| Control | Peptidoglycan | 1.257 | 245.94 +/− 49.86 | 219.21 |
| MAST4 | Peptidoglycan | 0.18 | 175.30 +/− 24.16 | 142.36 |

Table 2 also shows the production of inflammatory cytokine, IL-8 in response to the peptidoglycan challenge in the different cell populations. In control siRNA transfected keratinocytes, peptidoglycan challenge results in >9-fold increase in IL-8 production. In contrast, cells transfected with the MAST4 kinase siRNA duplex show a more modest 5-fold induction of IL-8 in response to the peptidoglycan challenge. This data shows that an 80% knockdown of MAST4 at the gene expression level is accompanied by a 35% reduction at the functional level, in the IL-8 response to peptidoglycan challenge. This data supports a key role for MAST4 in epidermal keratinocyte inflammatory signalling in response to a TLR2 agonist and demonstrates for the first time that inhibition of the MAST4 kinase can reduce inflammatory response to a microbial challenge in an in vitro epidermal model of skin inflammation.

Example 3—Epigenetic Study

In this example, the inventors conducted a genome-wide study of DNA methylation in human scalp biopsies taken from healthy and dandruff volunteers, to investigate whether there are epigenetic differences associated with dandruff.

Subjects

Subjects were female, UK residents of a northern European ancestry (Caucasian) and aged 23 to 37. Dandruff sufferers were defined as current anti-dandruff users, self-reported to have had dandruff for at least two years, and as had signs of dandruff during a visual assessment (Harding et al., Arch Dermatol Res (2002) 294:221-230) after 5 weeks use of a non-dandruff beauty shampoo. Healthy subjects were defined as not currently using anti-dandruff shampoo, did not report having dandruff for 2 years, and had no signs of dandruff after 5 weeks use of a non-dandruff beauty shampoo.

Samples and Analysis 4 mm scalp biopsies were taken from healthy (n=25) and dandruff (n=23) scalps and snap frozen on dry ice. DNA was extracted using a standard Phenol Chloroform method (Molecular Cloning A laboratory manual, 3$^{rd}$ edition. Sambrook and Russell. Cold Spring Harbor Laboratory Press, 2001). DNA methylation was measured by first using the Zymo bi-sulphite conversion method (EPIC Methylation arrays: www.illumina.com) followed by interrogation on the Infinium methylation EPIC beadchip 850K arrays (Illumina). Statistical analysis of the chip data involved conversion of beta values to m-values (Du et al., BMC Bioinformatics 2010, 11:587). Raw m-value data were normalised using quantile normalisation and linear statistical models were used to identify probes that were differentially methylated regions between dandruff and healthy control subjects. After statistical filtering, beta-values were used to filter for a 5 percent difference between dandruff and healthy controls.

Findings

Differentially methylated sites were identified with statistical cut-offs of FDR adjusted p-value<0.05 and delta-beta>=5% (Du et al. 2010). At this level, 701 methylation sites were differentially methylated in dandruff relative to healthy samples. One of these differentially methylated sites was cg13811092 which is located at nucleotide 66010095 on chromosome 5 and another is cg03133881 which is located at nucleotide 46467354 on chromosome 1 in human genome assembly GRCh37/hg37. This former site is located within intron 1 of the MAST4 gene and is significantly hypo-methylated in dandruff compared with healthy scalps; this site lies in a region of 'open chromatin' close to an enhancer element (so there are likely to be transcription factors binding to this site in scalp) and 10 kb upstream of rs58331610, the genetic variant identified in the genome wide association study of seborrheic dermatitis. The latter CpG site is significantly hypo-methylated in dandruff compared with health scalps. The site is located within intron 6 of the MAST2 gene, and is also within a region of 'open chromatin'.

In the literature, it is well documented that hypo-methylation within a regulatory region of a gene can be associated with altered expression of the gene and, as a result, its function (Bonder et al. Nat Genet. 2017 January; 49(1):131-138). Therefore, the presence of differentially methylated sites in the MAST4 and MAST2 genes is supportive evidence that these genes play a role in dandruff etiology, particularly when they coincide with a regulatory region such as a site of open chromatin.

The invention claimed is:

1. A method of treating an inflammatory skin condition in a mammalian subject that has a bacterial skin infection, the method comprising administering to the mammalian subject an effective dose of a short interfering RNA molecule that down-regulates the expression of a MAST4 gene.

2. The method of claim 1, wherein the skin condition comprises dandruff.

3. The method of claim 1, wherein the short interfering RNA molecule is essentially identical in sequence to a portion of the MAST4 gene transcript.

4. The method of claim 3, wherein the short interfering RNA molecule comprises a 20 to 30 nucleotide sequence identical to a portion of the MAST4 gene transcript.

5. The method of claim 1, wherein a formulation comprising the effective dose of the short interfering RNA molecule in admixture with a dermatologically acceptable bulking agent, diluent, carrier or excipient is administered to the mammalian subject, and wherein the mammalian subject is a human subject.

6. The method of claim 5, wherein the formulation comprises a skin penetration enhancer.

7. The method of claim 5, wherein the formulation is in the form of liquid, cream, gel, lotion, paste or patch.

8. The method of claim 5, wherein the formulation is in the form of a shampoo and/or a conditioner.

9. The method of claim 1, wherein the inflammatory skin condition is selected from the group consisting of atopic dermatitis (AD), psoriasis (PSO), seborrheic dermatitis, dandruff, rosacea, and acne.

10. A method of preventing an inflammatory skin condition in a mammalian subject that has a bacterial skin infection, the method comprising administering to the mammalian subject an effective dose of a short interfering RNA molecule that down-regulates the expression of a MAST4 gene.

11. The method of claim 10, wherein the skin condition comprises dandruff.

12. The method of claim 10, wherein the short interfering RNA molecule is essentially identical in sequence to a portion of the MAST4 gene transcript.

13. The method of claim 10, wherein the short interfering RNA molecule comprises a 20 to 30 nucleotide sequence identical to a portion of the MAST4 gene transcript.

14. The method of claim 10, wherein a formulation comprising the effective dose of the short interfering RNA molecule in admixture with a dermatologically acceptable bulking agent, diluent, carrier or excipient is administered to the mammalian subject, and wherein the mammalian subject is a human subject.

15. The method of claim 14, wherein the formulation comprises a skin penetration enhancer.

16. The method of claim 14, wherein the formulation is in the form of liquid, cream, gel, lotion, paste or patch.

17. The method of claim 14, wherein the formulation is in the form of a shampoo and/or a conditioner.

18. The method of claim 10, wherein the inflammatory skin condition is selected from the group consisting of atopic dermatitis (AD), psoriasis (PSO), seborrheic dermatitis, dandruff, rosacea, and acne.

19. A method of treating a microbial-induced inflammatory skin condition in a mammalian subject in need thereof, the method comprising administering to the mammalian subject an effective dose of a substance that down-regulates the expression of a MAST4 gene, wherein (a) the substance acts at the nucleic acid level, down-regulating the transcription of the MAST4 gene and/or the translation of the MAST4 gene transcript;
(b) the substance is a short interfering RNA molecule or a CRISPR-Cas component; and
(c) the inflammatory skin condition is selected from the group consisting of atopic dermatitis (AD), psoriasis (PSO), seborrheic dermatitis, dandruff, rosacea, and acne.

* * * * *

SEQUENCE LISTING

```
<160> NUMBER OF SEQ ID NOS: 1

<210> SEQ ID NO 1
<211> LENGTH: 1001
<212> TYPE: DNA
<213> ORGANISM: Homo sapiens
<220> FEATURE:
<221> NAME/KEY: variation
<222> LOCATION: (501)..(501)
<223> OTHER INFORMATION: site of variation where the allele is either A
``` or G

<400> SEQUENCE: 1

```
cccactttac caagcaaggt attaattttc ttcctagcag aggaaagagc tcagttcact        60
gtattctctt tccttttaca acagttacaa caacatttga ttcgtgatat tttagttgta       120
ggttgttgat ttaaaaatac acttagaagg tgtggagcac agaggaatac agggcatgat       180
tttgtgtatt gacctgtcaa ccctggttaa ctagcatgtc acaaaacaag ttctaaactc       240
aaatacagta aattatccag gtgggattct ggccacttgt gatgagttac ggattttgat       300
ttggatcatt cttgccctag cttggtaaca ggggagtgta tttatgtatt atgaaatgtg       360
agaccttttc aaatagtatt atggtcatgt gtcactcatg aatggggata tgttctgaga       420
agcatgtcat taagcaattt tgtcatttcg caaacatcat ggagtgtact tctacaaact       480
tagatggtgt agcttactac rtacctaggc tatatgtgtat agcctattgc tactgggcta       540
caaacctgta tagcttgtta ctgtactgaa tactgtaagc agttgtaaca caatcataag       600
tatttttata tctaaatgta tccaaacata gaaaaggtac agcaaaaata tggtattata       660
atcttttata atatataatt ataatatatg tgggctgtgg ttggttgaaa cattatacag       720
cactgactgt atcttaaatg gtcaataatt tttacttaaa gaaatcttac tagttgatgg       780
cttcaaagat taggctccct ctataggcca cagccatccc tttgtttctt tttgcatgtt       840
cttttctttt tgagaatgct taaaattatt atttccttat ttttcagcta attctgcctt       900
gttcttaatg aaatattatt tcattttaaa gaaatagtgg tgtttctggt catatgattt       960
ttctgttttt ttaattttta aatttctgcc aattttgttc a                          1001
```